United States Patent
Kojima et al.

(10) Patent No.: US 7,713,036 B2
(45) Date of Patent: May 11, 2010

(54) ROLLER-TYPE LIQUID PUMPING APPARATUS WITH IMPROVED INSTALLATION CAPABILITY

(75) Inventors: Seiji Kojima, Gunma (JP); Kenji Sugaya, Gunma (JP)

(73) Assignee: Japan Servo Co., Ltd., Tokyo (JP)

( * ) Notice: Subject to any disclaimer, the term of this patent is extended or adjusted under 35 U.S.C. 154(b) by 402 days.

(21) Appl. No.: 11/233,610

(22) Filed: Sep. 23, 2005

(65) Prior Publication Data

US 2006/0067845 A1 Mar. 30, 2006

(30) Foreign Application Priority Data

Sep. 29, 2004 (JP) ............................. 2004-283911

(51) Int. Cl.
*F04B 43/12* (2006.01)
(52) U.S. Cl. .................................. 417/477.5; 417/477.3
(58) Field of Classification Search ................. 417/476, 417/477.3, 477.5, 477.7, 477.8
See application file for complete search history.

(56) References Cited

U.S. PATENT DOCUMENTS

| | | | | |
|---|---|---|---|---|
| 2,831,437 A | * | 4/1958 | Cromwell et al. | 417/477.5 |
| 3,737,257 A | * | 6/1973 | DeVries | 417/477.8 |
| 3,918,854 A | * | 11/1975 | Catarious et al. | 417/477.11 |
| 3,938,909 A | * | 2/1976 | Willock | 417/12 |
| 4,095,923 A | | 6/1978 | Cullis et al. | |
| 4,135,746 A | * | 1/1979 | Sterling | 292/92 |
| 4,558,996 A | * | 12/1985 | Becker | 417/374 |
| 4,832,585 A | | 5/1989 | Horiuchi et al. | |
| 6,626,867 B1 | | 9/2003 | Christenson et al. | |

FOREIGN PATENT DOCUMENTS

| | | |
|---|---|---|
| JP | 61-268887 | 11/1986 |
| JP | 08-247039 | 9/1996 |
| JP | 2002-266775 | 9/2002 |

OTHER PUBLICATIONS

Author: Nicholas P. Chironis, Title: "Mechanisms, Linkages, and Mechanical Controls", Imprint in 1965, Publisher: Mc-Graw-Hill, Inc., p. 156—Figure 2.*

* cited by examiner

*Primary Examiner*—Devon C Kramer
*Assistant Examiner*—Dnyanesh Kasture
(74) *Attorney, Agent, or Firm*—Boyle Fredrickson, S.C.

(57) ABSTRACT

A liquid pumping apparatus comprising a rotor housing, a rotor having at least one roller, to be rotated by a prime mover, an inner periphery wall of the rotor housing, a flexible tube to be inserted into a gap formed between the rotor and the inner periphery wall and squeezed when the rotor is rotated so as to transfer a liquid fed into the tube, and a deformable guide for guiding the flexible tube in a moving path of the roller. At least one portion of the inner periphery wall is movable so as to approach or separate from the rotor.

9 Claims, 4 Drawing Sheets

ROLLER-TYPE LIQUID PUMPING APPARATUS WITH IMPROVED INSTALLATION CAPABILITY

BACKGROUND OF THE INVENTION

1. Field of the Invention

The present invention relates to a liquid pumping apparatus, and more particularly, relates to a liquid pumping apparatus for pumping a liquid, such as chemicals or blood etc. into a human body by revolving rollers rotated by a prime mover to compress a flexible tube to thereby force the liquid through the flexible tube.

2. Description of the Prior Art

A liquid pumping apparatus, wherein a flexible tube is inserted into a clearance formed between a fixed inner periphery wall and revolving rollers to compress the flexible tube and thereby force a liquid through the flexible tube is described in the Japanese Patent Application Laid-Open No. 268887/86, for example.

However, in such prior art, it is necessary to slowly insert the flexible tube into the clearance while rotating a rotor having the rollers, because the clearance is so small that the flexible tube is collapsed fully. Accordingly, installation of the flexible tube requires an undesirable amount of time and labor.

Further, it is necessary to use a large force for removing the flexible tube from the small clearance formed between the fixed inner periphery wall and the revolving rollers, so that the flexible tube is liable to be damaged.

In case that guide rollers are provided on the outer peripheral surface of the rotor in order to guide the flexible tube in a moving path of the rollers, the flexible tube is contacted and damaged by the guide rollers when the flexible tube is inserted into the clearance.

SUMMARY OF THE INVENTION

Accordingly, it is an object of this invention to provide a liquid pumping apparatus free from the above defects.

Another object of the present invention is to provide a liquid pumping apparatus comprising a rotor housing, a rotor having at least one roller, to be rotated by a prime mover, an inner periphery wall of the rotor housing, a flexible tube to be inserted into a gap formed between the rotor and the inner periphery wall and squeezed when the rotor is rotated so as to transfer a liquid fed into the tube, and a deformable guide for guiding the flexible tube in a moving path of the roller.

A further, object of the present invention is to provide a liquid pumping apparatus, wherein at least one portion of the inner periphery wall is movable so as to approach or separate from the rotor.

Yet further object of the present invention is to provide a liquid pumping apparatus, wherein the guide is supported by one end of a guide shaft, the guide shaft being supported by the rotor so as to incline with respect to the rotor, and an arcuate groove is formed in the rotor, the other end of the guide shaft being movable along the arcuate groove.

Another object of the present invention is to provide a liquid pumping apparatus, wherein the guide is supported by a guide shaft formed of a bendable resilient member.

These and other aspects and objects of the present invention will be better appreciated and understood when considered in conjunction with the following description and the accompanying drawings. It should be understood, however, that the following description, while indicating preferred embodiments of the present invention, is given by way of illustration and not of limitation. Many changes and modifications may be made within the scope of the present invention without departing from the spirit thereof, and the invention includes all such modifications.

DESCRIPTION OF THE PREFERRED EMBODIMENTS

Figure 1:
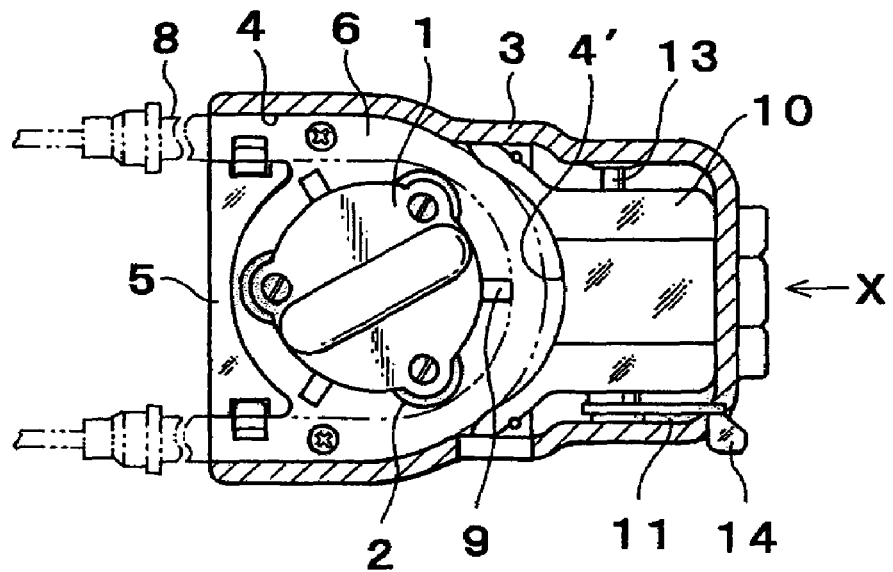
FIG. 1 is a horizontally sectioned plan view of a liquid pumping apparatus according to the present invention.
Figure 2:
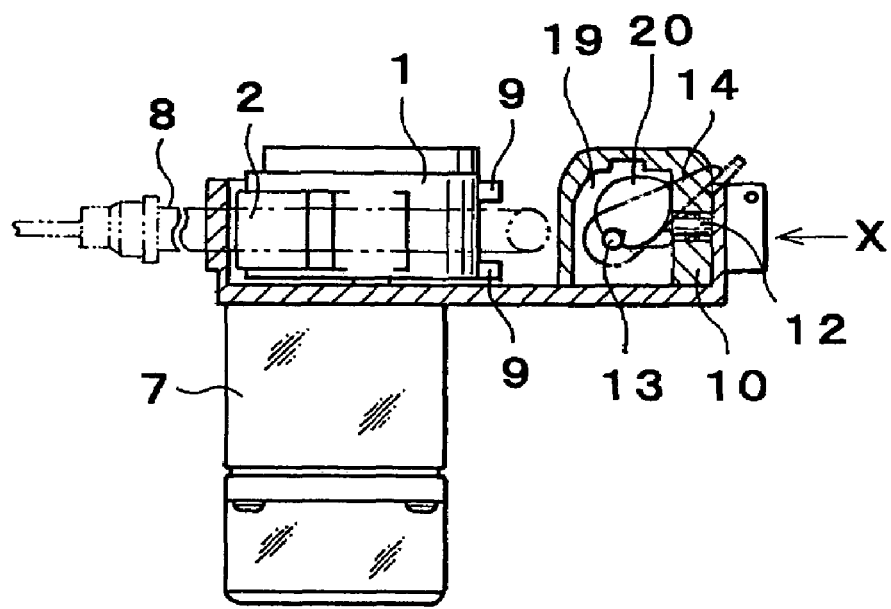
FIG. 2 is a vertically sectioned front view of the liquid pumping apparatus shown in FIG. 1.

FIG. 1 and FIG. 2 show a liquid pumping apparatus according to the present invention. In FIG. 1 and FIG. 2, a reference numeral 1 denotes a plate-like rotor, 2 denote a plurality of rollers rotatably supported on the rotor 1. The rollers 2 are separated to one another along a circle and a portion of each roller 2 is projected from an outer peripheral surface of the rotor 1 reference numeral 3 denotes a rotor housing, 4 denotes a U-shaped inner surface of the housing 3 surrounding the rotor 1, 10 denotes a slidable body arranged in the rotor housing 3 movably along a guide rod 12 by a slide means 11, 4' denotes an arcuate surface formed on the slidable body 10 so as to face to the outer peripheral surface of the rotor 1, 5 denotes an opening formed at one end of the housing 3, 6 denotes a clearance or gap formed between the rotor 1 and the arcuate surface 4', 7 denotes a prime mover for rotating the rotor 1, 8 denotes a flexible tube, a portion of which is inserted into the gap 6 so as to surround the rotor 1, and 9 denote a deformable guide rollers for guiding and positioning the portion of the flexible tube 8 at a normal moving path of the roller 2 in the gap 6.

The slide means 11 comprises a cavity 19 formed in the movable body 10, a rotary shaft 13 extending through the cavity 19, supported rotatably by the housing 3, a heart-shaped cam 20 arranged in the cavity 19 and fixed at a base portion thereof to the rotary shaft 13, and a lever 14 fixed at a base portion thereof to the rotary shaft 13.

Figure 3:
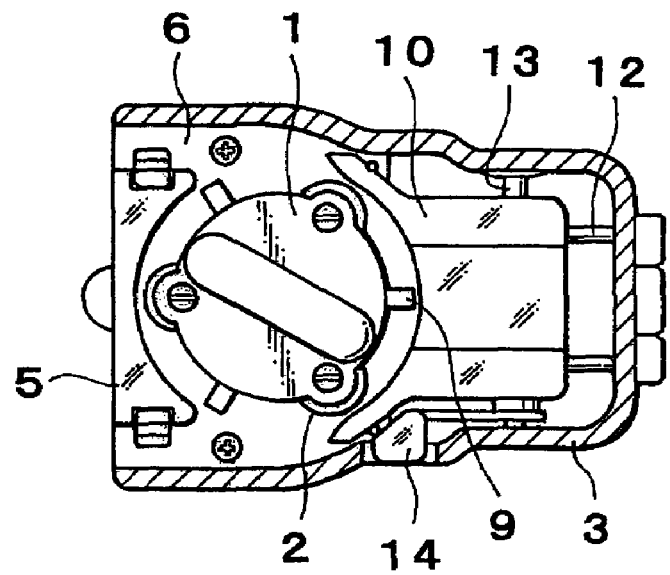
FIG. 3 is a horizontally sectioned plan view of the liquid pumping apparatus in an operating state.
Figure 4:
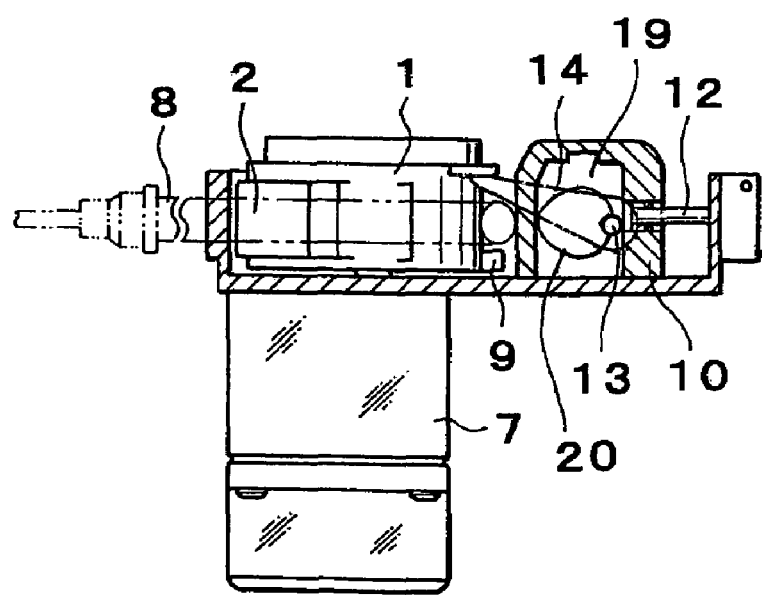
FIG. 4 is a vertically sectioned front view of the liquid pumping apparatus shown in FIG. 3.

The movable body 10 is moved within the housing 3 in a direction X shown in FIG. 1 and FIG. 2 when the lever 14 is rotated in the counter clockwise direction centering around the rotary shaft 13. Specifically, the cam 20 is rotated in the counter clockwise direction in the cavity 19, so that a top portion of the cam 20 pushes the movable body 10 and the arcuate surface 4' is approached to the rotor 1 as shown in FIG. 3 and FIG. 4. As a result, the portion of the flexible tube 8 inserted into the gap 6 is compressed between the roller 2 and the arcuate surface 4' of the slidable body 10. Accordingly, the portion of the flexible tube 8 is squeezed by the roller 2 when the rotor 1 is rotated, so that the liquid fed into the tube 8 is transferred.

Figure 5:
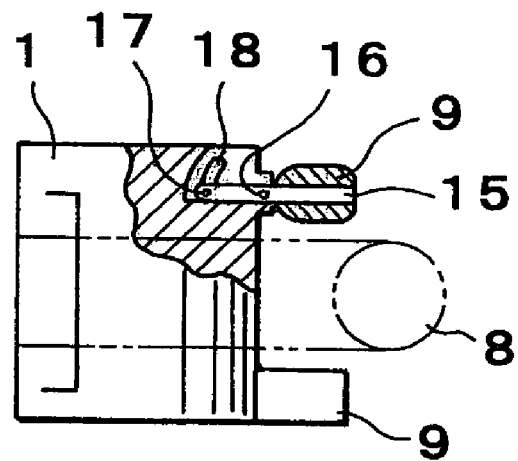
FIG. 5 is an enlarged front view of an embodiment of a guide roller of the liquid pumping apparatus according to the present invention.
Figure 6:
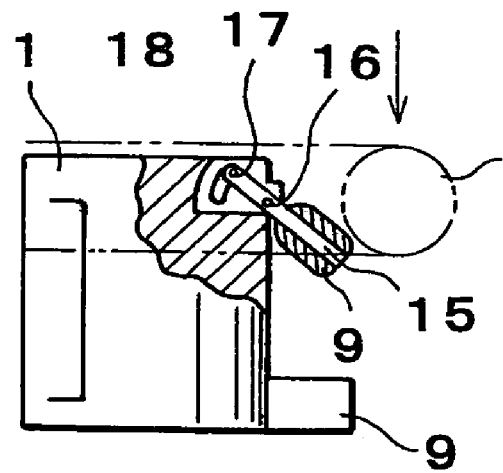
FIG. 6 is an enlarged front view of the guide roller shown in FIG. 5 in an operating state.

As shown in FIG. 5, the guide roller 9 is held by one end of a guide shaft 15. The guide shaft 15 is supported at the center thereof by an outer peripheral surface of the rotor 1 through a center pin 16 so as to incline with respect to the rotor 1. An arcuate groove 18 extending centering around the pin 16 is formed in the rotor 1. The other end of the guide shaft 15 is engaged slidably with the groove 18 through a guide pin 17. The guide roller 9 is brought into contact with the flexible tube 8 when the flexible tube 8 is moved toward the gap 6 and then inclined as shown in FIG. 6. The guide roller 9 is returned to the original position by a return spring (not shown) etc., when the flexible tube 8 is arranged at the normal moving path in the gap 6 as shown in FIG. 5.

Figure 7:
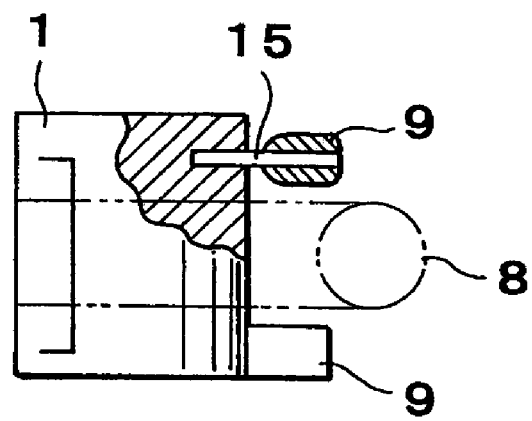
FIG. 7 is an enlarged front view of the other embodiment of a guide roller of the liquid pumping apparatus of the present invention.
Figure 8:
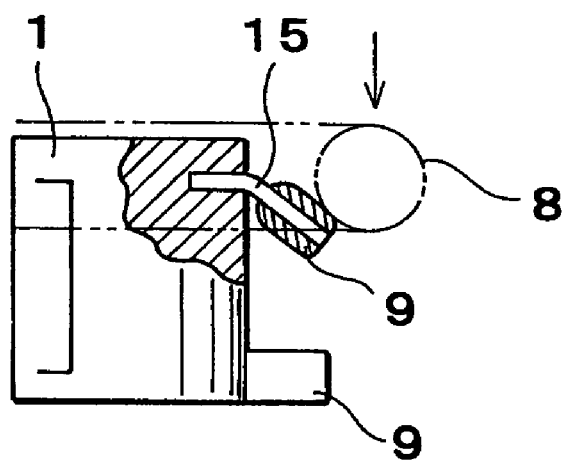
FIG. 8 is an enlarged front view of the guide roller shown in FIG. 7 in an operating state.

In the other embodiment of the present invention, the guide shaft 15 is formed of a bendable resilient member fixed to an outer peripheral portion of the rotor 1, and the center pin 16, the guide pin 17 and the arcuate groove 18 are omitted as shown in FIG. 7. The guide shaft 15 is bent when the flexible tube 8 is moved toward the gap 6 as shown in FIG. 8.

According to the liquid pumping apparatus of the present invention, the slidable body 10 is moved in a direction opposite to the direction X and a large gap is formed between the outer peripheral surface of the rotor 1 and the arcuate surface 4' of the slidable body 10, when the lever 14 is rotated in the clockwise direction centering around the rotary shaft 13 from the position shown in FIG. 4 to the position shown in FIG. 2. Thus, the flexible tube 8 can be inserted easily in the gap 6 and the operation ability can be enhanced.

Further, the flexible tube 8 can be guided into the gap 6 by the guide roller 9 which is inclined or bent when it is brought into contact with the flexible tube 8, so that the flexible tube 8 is prevented from being damaged.

The lever 14 can be operated by hand or electrically. A reaction force applied to the slidable body 10 during the squeezing operation of the flexible tube 8 can be received by the rotary shaft 13 by directing the vector of the reaction force to the rotary center of the cam 20.

As stated above, according to the present invention, the gap 6 formed between the outer peripheral surface of the rotor 1 and the arcuate surface 4' of the slidable body 10 can be enlarged easily and the operation ability can be enhanced. Further, the flexible tube can be prevented from being damaged when it is inserted into the gap 6 or removed from the gap 6.

While this invention has been described with specific embodiments thereof, it is evident that many alternatives, modifications, and variations will be apparent to those skilled in the art. Accordingly, the preferred embodiments of the invention as set forth herein are intended to be illustrative, not limiting. Various changes may be made without departing from the spirit and scope of the invention. The scope of the present invention should be defined by the terms of the claims appended hereto.

We claim:

1. A roller-type liquid pumping apparatus with improved installation capability, comprising:
    a rotor housing having an inner periphery wall, a rotor having at least one roller rotated by a prime mover, a flexible tube inserted into a gap formed between the rotor and the inner periphery wall of the rotor housing and squeezed when the rotor is rotated so as to transfer a liquid fed into the tube, and a guide for guiding the flexible tube in the moving path of the roller, wherein at least one portion of the inner periphery wall of the rotor housing is movable so as to approach and separate from the rotor, wherein the guide is supported by one end of a guide shaft, the guide shaft being supported by an arcuate groove in the rotor so as to move along the arcuate groove and to incline against the force of a return spring with respect to the rotor, and wherein the guide moves along an arcuate path when the tube is inserted.

2. A roller-type liquid pumping apparatus with improved installation capability, comprising:
    a rotor housing having an inner periphery wall,
    a rotor having at least one roller rotated by a prime mover and having an arcuate groove formed therein,
    a flexible tube which is inserted into a gap formed between the rotor and an inner periphery wall of the rotor housing and which is squeezed when the rotor is rotated so as to transfer a liquid fed into the tube,
    a guide shaft,
    a guide for guiding the flexible tube in the moving path of the roller, the guide supported by one end of the guide shaft, and
    a return spring that operatively engages the guide, wherein
        at least one portion of the inner periphery wall of the rotor housing is movable toward and away from the rotor, wherein
        another end of the guide shaft is supported by the arcuate groove in the rotor so as to move along the arcuate groove and to incline, against the force of the return spring, with respect to the rotor, and wherein
        the guide moves along an arcuate path when the tube is inserted.

3. The roller-type liquid pumping apparatus of claim 2, further comprising:
    a center pin that rotatably secures the guide shaft to the rotor housing; and
    a guide pin disposed at an end of the guide shaft and slidably engaging the arcuate groove.

4. The roller-type liquid pumping apparatus of claim 2, wherein the flexible tube moves the guide downwardly through the gap, and wherein the return spring biases the guide upwardly so that the guide moves upwardly through the gap to a first position after the tube has been inserted.

5. A roller-type liquid pumping apparatus with improved installation capability, comprising:
    a rotor having at least one roller rotated by a prime mover,
    a rotor housing having an inner periphery wall, wherein at least one portion of the inner periphery wall is movable toward and away from the rotor,
    a flexible tube which is inserted into a gap formed between the rotor and an inner periphery wall of the rotor housing and which is squeezed when the rotor is rotated so as to transfer a liquid fed into the tube,
    a guide shaft supported at a first end thereof by the rotor, and
    a guide supported by a second end of the guide shaft for guiding the flexible tube, wherein the guide moves along an arcuate path when the tube is inserted.

6. The roller-type liquid pumping apparatus of claim 5, wherein the guide moves downwardly through the gap and inwardly toward the rotor when the tube is inserted.

7. The roller-type liquid pumping apparatus of claim 5, further comprising
    an arcuate groove in the rotor for receiving the first end of the guide shaft, wherein the guide shaft is rotatably attached to the rotor so that the first end of the guide shaft moves along the arcuate groove when the tube is inserted.

8. The roller-type liquid pumping apparatus of claim 5, further comprising a spring that is operably coupled with the guide shaft so as to return the guide shaft to a first position after the tube is inserted into the gap.

9. The roller-type liquid pumping apparatus of claim 5, wherein the guide shaft is a bendable resilient member fixed to an outer peripheral portion of the rotor.

* * * * *